(12) United States Patent
Oh et al.

(10) Patent No.: US 12,306,372 B2
(45) Date of Patent: May 20, 2025

(54) LENS AND LENS ASSEMBLY INCLUDING THE SAME

(71) Applicant: SAMSUNG ELECTRO-MECHANICS CO., LTD., Suwon-si (KR)

(72) Inventors: Hae Sung Oh, Suwon-si (KR); Ae Rim Kim, Suwon-si (KR); Sang Hyun Kwon, Suwon-si (KR); Sang Hyeon Hong, Suwon-si (KR); Sang A Kim, Suwon-si (KR)

(73) Assignee: Samsung Electro-Mechanics Co., Ltd., Suwon-si (KR)

( * ) Notice: Subject to any disclaimer, the term of this patent is extended or adjusted under 35 U.S.C. 154(b) by 594 days.

(21) Appl. No.: 17/744,078

(22) Filed: May 13, 2022

(65) Prior Publication Data
US 2023/0221464 A1    Jul. 13, 2023

(30) Foreign Application Priority Data
Jan. 11, 2022  (KR) .......................... 10-2022-0003805

(51) Int. Cl.
| | | |
|---|---|---|
| G02B 1/04 | (2006.01) | |
| C07C 9/14 | (2006.01) | |
| C07C 69/14 | (2006.01) | |
| G02B 3/00 | (2006.01) | |
| G02B 5/26 | (2006.01) | |

(52) U.S. Cl.
CPC .............. *G02B 1/041* (2013.01); *C07C 9/14* (2013.01); *C07C 69/14* (2013.01); *G02B 3/00* (2013.01); *G02B 5/26* (2013.01)

(58) Field of Classification Search
CPC ............ G02B 1/041; G02B 3/00–3/14; G02B 5/00–5/32; G02B 27/0018; G02B 27/0025; C09B 1/00–1/62; C07C 9/14; C07C 69/14
See application file for complete search history.

(56) References Cited

U.S. PATENT DOCUMENTS

| | | | |
|---|---|---|---|
| 12,055,734 | B2 | 8/2024 | Park et al. |
| 2003/0182737 | A1 | 10/2003 | Inoue et al. |

(Continued)

FOREIGN PATENT DOCUMENTS

| | | |
|---|---|---|
| CN | 114167527 A | 3/2022 |
| CN | 115708002 A | 2/2023 |

(Continued)

OTHER PUBLICATIONS

Korean Office Action issued on Apr. 28, 2023, in counterpart Korean Patent Application No. 10-2022-0003805 (7 pages in English, 5 pages in Korean).

(Continued)

*Primary Examiner* — Prashant J Khatri
(74) *Attorney, Agent, or Firm* — NSIP Law

(57) ABSTRACT

A lens includes an optical portion; and a rib portion extending to an external side of the optical portion in a radial direction and including a light transmitting region and a light-shielding region, wherein the light-shielding region includes an ester-based compound and a hydrocarbon-based compound, and wherein the hydrocarbon-based compound includes a saturated hydrocarbon compound.

19 Claims, 14 Drawing Sheets

(56) References Cited

U.S. PATENT DOCUMENTS

| | | |
|---|---|---|
| 2008/0124555 A1 | 5/2008 | Klun et al. |
| 2012/0154811 A1 | 6/2012 | Pokorny et al. |
| 2016/0011415 A1 | 1/2016 | Takada |
| 2021/0072589 A1* | 3/2021 | Taguchi .................. C09D 4/00 |
| 2022/0001418 A1 | 1/2022 | Park et al. |
| 2022/0075096 A1 | 3/2022 | Park et al. |
| 2023/0055901 A1 | 2/2023 | Park et al. |

FOREIGN PATENT DOCUMENTS

| | | |
|---|---|---|
| JP | 2939305 B2 | 8/1999 |
| JP | 4742648 B2 | 8/2011 |
| JP | 5807139 B2 | 11/2015 |
| KR | 10-0553012 B1 | 2/2006 |
| KR | 10-2018-0134984 A | 12/2018 |
| KR | 10-2019-0021493 A | 3/2019 |
| KR | 10-2023-0027976 A | 2/2023 |

OTHER PUBLICATIONS

Chinese Office Action issued on Apr. 10, 2025, in corresponding Chinese Patent Application No. 202210817730.5. (5 pages in English, 10 pages in Chinese).

* cited by examiner

LENS AND LENS ASSEMBLY INCLUDING THE SAME

CROSS-REFERENCE TO RELATED APPLICATIONS

This application claims the benefit under 35 U.S.C. 119(a) of Korean Patent Application No. 10-2022-0003805 filed on Jan. 11, 2022, in the Korean Intellectual Property Office, the entire disclosure of which is incorporated herein by reference for all purposes.

BACKGROUND

1. Field

The present disclosure relates to a lens and a lens assembly including the same.

2. Description of the Background

When a fluorescent light or strong light at a certain angle in a dark room is incident to a lens included in a camera module internal reflection from a rib surface of the lens may occur, or light at a specific angle may cause internal reflection from a rib surface of the lens. The light may not be related to image formation and may cause flares or ghosting on a screen. Accordingly, it may be necessary to block unnecessary light incident to a rib surface of a lens.

The above information is presented as background information only to assist with an understanding of the present disclosure. No determination has been made, and no assertion is made, as to whether any of the above might be applicable as prior art with regard to the disclosure.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a lens includes an optical portion, and a rib portion extending to an external side of the optical portion in a radial direction and including a light transmitting region and a light-shielding region, wherein the light-shielding region includes an ester-based compound and a hydrocarbon-based compound, and wherein the hydrocarbon-based compound includes a saturated hydrocarbon compound.

The saturated hydrocarbon compound may include a C6-C10 saturated hydrocarbon chain compound.

The C6-C10 saturated hydrocarbon chain compound may include at least one of hexane, heptane, and decane.

The ester-based compound may include a glycol ether acetate compound.

The glycol ether acetate compound may include at least one of propylene glycol monomethyl ether acetate, ethylene glycol monobutyl ether acetate, and diethylene glycol monoethyl ether acetate.

The light-shielding region may further include a light-shielding dye.

The light-shielding dye may include at least one non-polar dye of a non-polar azo dye and a non-polar anthraquinone dye.

The lens may include at least one of a polycarbonate-based compound and a polyolefin-based compound.

The light-shielding region may be disposed in the rib portion.

The light-shielding region may be disposed on an inner side of at least one surface of the rib portion in an optical axis direction.

The light-shielding region may be disposed on an inner side of a partial region of at least one surface of the rib portion in the optical axis direction.

The light-shielding region may further be disposed on an inner side of a surface of the rib portion in the radial direction.

In another general aspect, a lens assembly includes a lens barrel including an internal space, and one or more lenses stacked along an optical axis in the internal space of the lens barrel, wherein at least one lens of the one or more lenses includes an optical portion and a rib portion extending to an external side of the optical portion in a radial direction and including a light transmitting region and a light-shielding region, wherein the light-shielding region includes an ester-based compound and a hydrocarbon-based compound, and wherein the hydrocarbon-based compound includes a saturated hydrocarbon compound.

The at least one lens may include a polycarbonate-based component or a polyolefin-based compound, and the light-shielding region may include propylene glycol monomethyl ether acetate and hexane, heptane, or decane.

The light-shielding region may further include at least one non-polar dye of a non-polar azo dye and a non-polar anthraquinone dye.

In another general aspect, a lens includes an optical portion, and a rib portion extending to an external side of the optical portion in a radial direction and comprising a light transmitting region and a light-shielding region, wherein the light-shielding region comprises a dye disposed in the rib portion, and wherein a concentration of the dye decreases in a direction away from a surface of the rib portion.

The light-shielding region may be disposed on an inner side of one surface of the rib portion in an optical axis direction, and the light transmitting region and the light-shielding region may be disposed in sequence in the optical axis direction.

The light-shielding region may include an ester-based compound and a hydrocarbon-based compound, and the hydrocarbon-based compound may include a saturated hydrocarbon compound.

Other features and aspects will be apparent from the following detailed description, the drawings, and the claims.

BRIEF DESCRIPTION OF DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
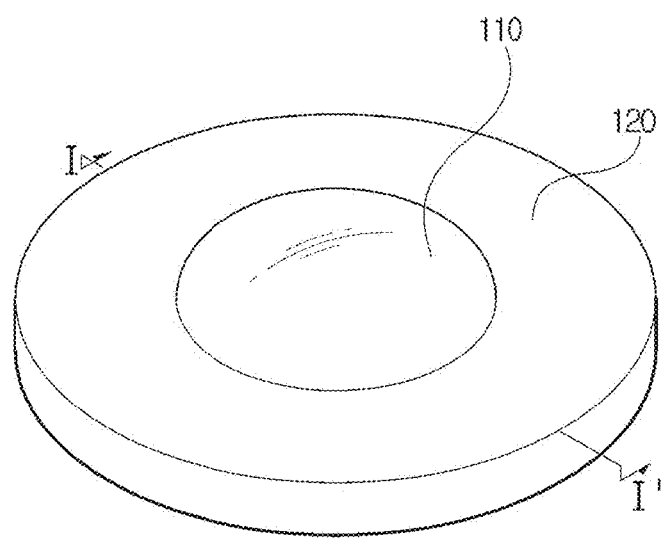
FIG. 1 is a perspective diagram illustrating a lens according to an example embodiment of the present disclosure.

Hereinafter, embodiments of the present disclosure will be described in detail as follows with reference to the accompanying drawings, it is noted that examples are not limited to the same.

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of this disclosure. For example, the sequences of operations described herein are merely examples, and are not limited to those set forth herein, but may be changed as will be apparent after an understanding of this disclosure, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of this disclosure.

Throughout the specification, when an element, such as a layer, region, or substrate is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items; likewise, "at least one of" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms, such as "above," "upper," "below," "lower," and the like, may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above," or "upper" relative to another element would then be "below," or "lower" relative to the other element. Thus, the term "above" encompasses both the above and below orientations depending on the spatial orientation of the device. The device may also be oriented in other ways (rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

Herein, it is noted that use of the term "may" with respect to an example, for example, as to what an example may include or implement, means that at least one example exists in which such a feature is included or implemented while all examples are not limited thereto.

The features of the examples described herein may be combined in various ways as will be apparent after an understanding of this disclosure. Further, although the examples described herein have a variety of configurations, other configurations are possible as will be apparent after an understanding of this disclosure.

An aspect of the present disclosure is to provide a lens in which at least a portion of a rib portion of polycarbonate-based and/or polyolefin-based optical polymer is blackened, and a lens assembly including the same.

Another aspect of the present disclosure is to provide a lens which may prevent flares and ghosting, and a lens assembly including the same.

An aspect of the present disclosure is to form a colored region by coloring at least a partial region of a rib portion of a lens using a coloring dye composition including an ester-based compound and a hydrocarbon-based compound.

In the drawings, an X direction may be defined as a first direction, an L direction, or a length direction, a Y direction may be defined as a second direction, a W direction, or a width direction, and a Z direction may be defined as a third direction, a T direction, a thickness direction, or an optical axis direction.

Lens

FIG. 1 is a perspective diagram illustrating a lens according to an example embodiment.

Figure 2:
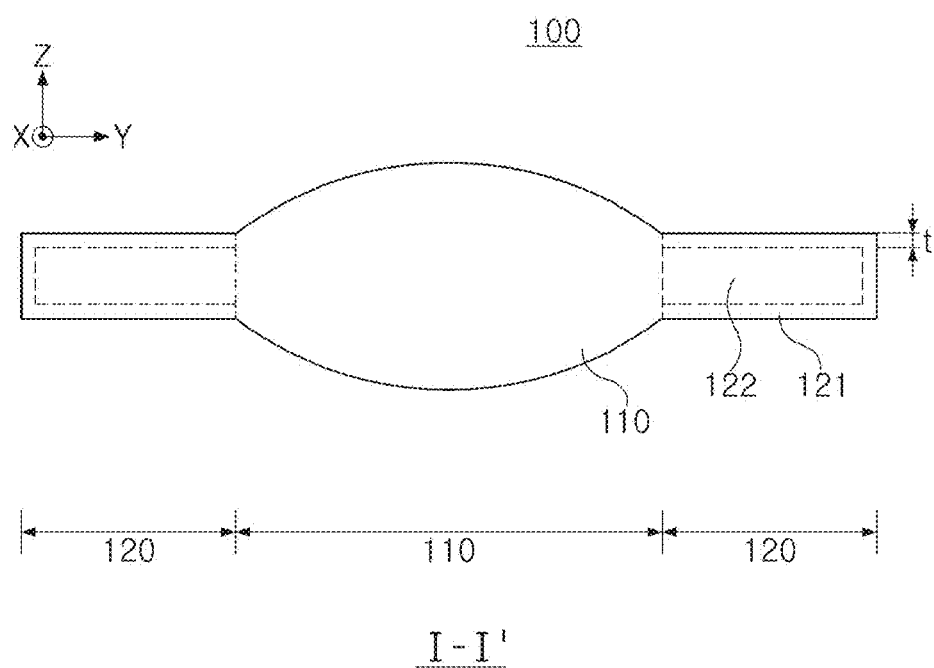
FIG. 2 is a cross-sectional diagram taken along line I-I' in FIG. 1.

FIG. 2 is a cross-sectional diagram taken along line I-I' in FIG. 1.

Figure 3:
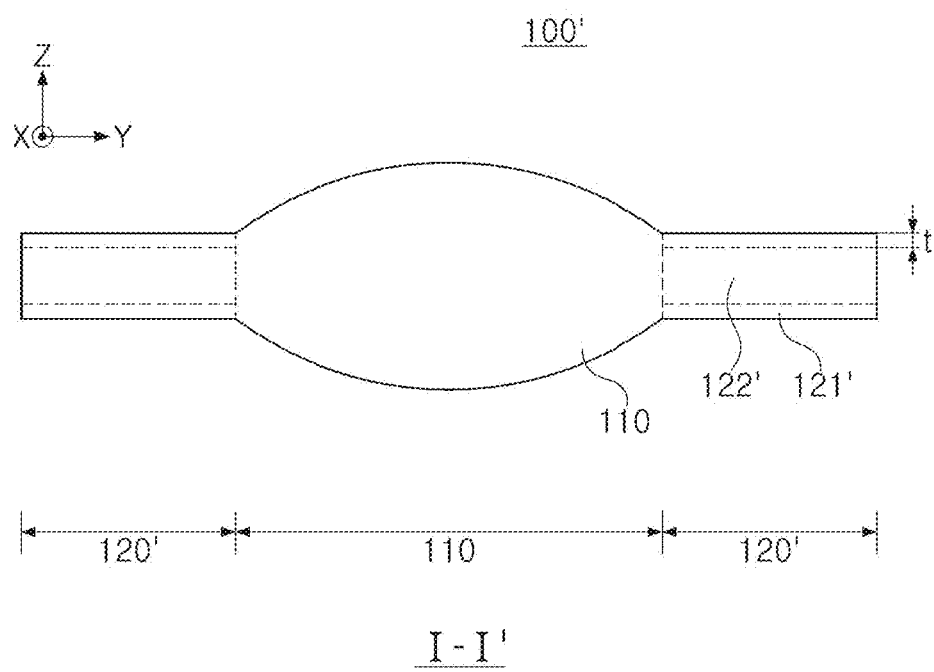
FIG. 3 is a cross-sectional diagram illustrating a modified example of FIG. 2.
Figure 4:
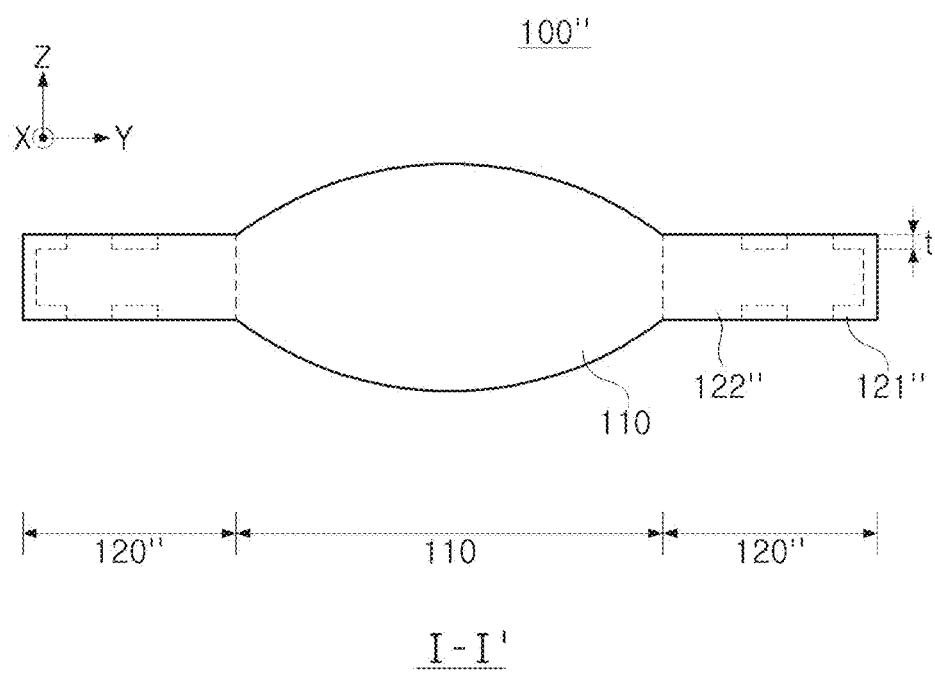
FIG. 4 is a cross-sectional diagram illustrating another modified example of FIG. 2.
Figure 5:
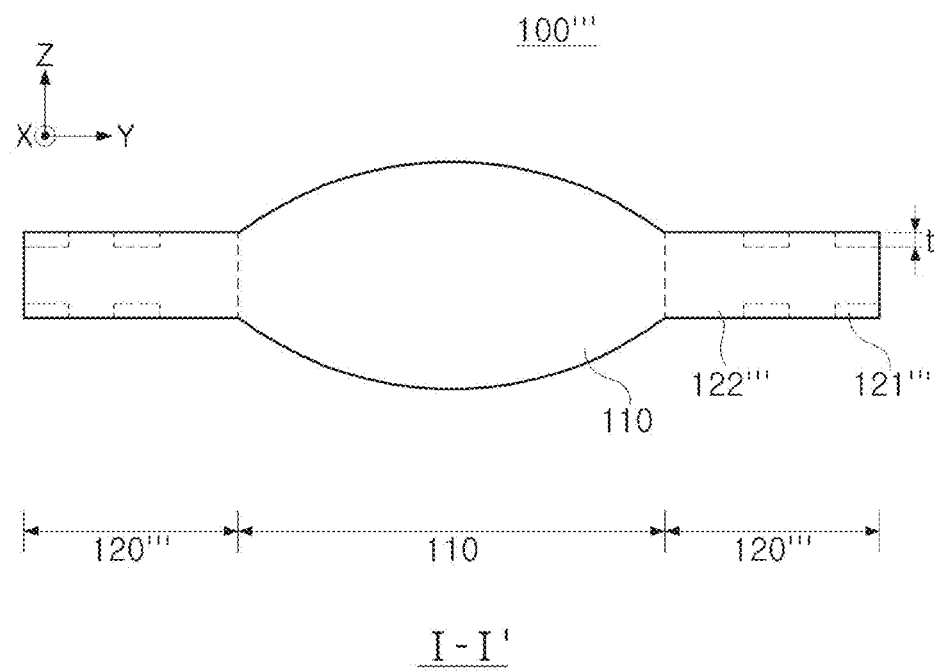
FIG. 5 is a cross-sectional diagram illustrating another modified example of FIG. 2.

FIGS. 3 to 5 are cross-sectional diagrams illustrating one or more modified examples of FIG. 2.

Referring to the drawings, a lens 100 according to an example may include an optical portion 110 and a rib portion 120 extending to an external side of the optical portion 110 in a radial direction.

The shape or type of the lens 100 may not be limited to any particular example, and a lens used in an optical device such as a camera module may be used. The lens 100 may be a plastic resin lens including a resin component, and a resin component may include, for example, a polycarbonate-based compound and/or a polyolefin-based compound. The lens 100 may be formed by forming a composition including such a resin component into a predetermined shape using a mold, but an example embodiment thereof is not limited thereto.

A polycarbonate-based compound may be a thermoplastic plastic polymer having a chain structure of bisphenol A and phosgene, and for example, a product of MITSUBISHI GAS CHEMICAL of Japan may be used. A refractive index of the polycarbonate-based compound is not limited to any particular example, and may be about 1.63 to 1.68.

The polyolefin-based compound may include at least one of a cycloolefin polymer and a cycloolefin copolymer, and for example, a product of MITSUI CHEMICALS and ZEON may be used. The polyolefin-based compound may be formed by polymerization of a cyclic monomer such as norbornene, but an example embodiment thereof is not limited thereto. A refractive index of the polyolefin-based compound is not limited to any particular example, and may be about 1.52 to 1.56.

The optical portion 110 may be a region in which optical performance of the lens 100 is exhibited. For example, the optical portion 110 may be a region in which light reflected from an object (or a subject) is refracted. The rib portion 120 may be a region for fixing the lens 100 to another component, such as, for example, a lens barrel, another lens, and/or a spacer. The rib portion 120 may be a region extending to an external side of the optical portion 110 in the radial direction. In the example embodiment, "radial direction" may refer to a direction from a center of the optical portion 110 toward an outer circumferential surface of the lens 100, and may refer to a direction perpendicular to the optical axis direction. The rib portion 120 and the optical portion 110 may be distinguished from each other by positions or functions thereof, and may be divided within the same lens. Accordingly, the optical portion 110 and the rib portion 120 may form an integrated lens.

The rib portion 120 may include a light transmitting region 122 and a light-shielding region 121. The light transmitting region 122 may refer to a region through which light may pass, and may refer to a region in which the light-shielding region 121 is not formed. The light-transmitting region 122 may refer to a region in which an average transmittance for light in a range of 400 nm to 650 nm may be more than 80%, for example, and the light-shielding region 121 may refer to a region in which an average transmittance for light in a range of 400 nm to 650 nm may be 20% or less, but an example embodiment thereof is not limited thereto. The terms "light transmitting region 122" and "light-shielding region 121" may be used to distinguish regions dyed with a non-polar dye and a non-dyed region from each other in the same lens, and the light transmitting region 122 and the light-shielding region 121 may not have clear boundaries therebetween.

The light-shielding region 121 may be disposed in the rib portion 120. In the example embodiment, the configuration in which a certain "region" is disposed in the rib portion indicates that a maximum dimension of the region in the first direction, the second direction and the third direction may be less than the maximum dimension of the rib portion in the first direction, the second direction and the third direction, and that the overall outer boundary of the region may be present in the rib portion. The lens 100 according to an example may form the light-shielding region 121 by coloring the rib portion 120 as described below, and accordingly, the light-shielding region 121 may be disposed in the rib portion 120.

The light-shielding region 121 may be disposed on an inner side of at least one surface of the rib portion 120 in the optical axis direction. In the example embodiment, the term "optical axis" may refer to a conceptual line indicating an optical path through which light passes, and may refer to an axis of symmetry when a curved surface of the lens has rotational symmetry. For example, referring to FIG. 2, assuming a conceptual Z axis passing through the center of the lens, the Z axis may be the optical axis, and the Z axis direction may refer to the optical axis direction. When the light-shielding region 121 is disposed on an inner side of one surface of the rib portion 120 in the optical axis direction, the light-shielding region 121 may be disposed on an inner side of at least one surface among both surfaces of the rib portion 120 in the Z axis direction. In this case, the lens may be dyed in only one direction, such that production efficiency may increase. When the light-shielding region 121 is disposed in inner sides of both surfaces of the rib portion 120 in the optical axis direction, the rib portion 120 may have a region in which the light-shielding region 121, the light-transmitting region 122, and the light-shielding region 121 are disposed in sequence in the Z-axis direction. In this case, since the light-shielding region 121 is disposed in inner sides of both surfaces of the rib portion 120 in the optical axis direction, light transmittance of the light-shielding region 121 of the rib portion 120 may be further reduced.

The light-shielding region 121 may be further disposed on an inner side of the surface of the rib portion 120 in the radial direction. The light-shielding region 121 may be further disposed on the surface of the rib portion 120 in the radial direction, that is, an outermost region of the rib portion 120 of the lens 100 in a direction perpendicular to the Z-axis direction. In this case, the light-shielding region 121 may be disposed on the surface of the rib portion 120 perpendicular to the optical axis, and accordingly, light entering in a direction other than the optical axis direction may be blocked, thereby effectively preventing lens flare or ghosting.

The light-shielding region 121 may be disposed in contact with at least one surface of the rib portion 120. The configuration in which the light-shielding region 121 is disposed in contact with the surface of the rib portion 120 may indicate that the light-shielding region 121 is disposed on an end of the rib portion 120 in the X-axis, Y-axis and/or Z-axis directions, that a spatial boundary of the rib portion 120 in the X-axis, Y-axis, and/or Z-axis direction may coincide with a spatial boundary of the light-shielding region 121 in the X-axis, Y-axis and/or Z-axis direction, and that the light-shielding region 121 may be exposed to the surface of the rib portion 120. In the lens 100 according to an example, the rib portion 120 may be colored using a non-polar dye, and accordingly, an additional structure such as a coating layer is not disposed on an external region, such that an excellent balance may be obtained.

An average thickness t of the light-shielding region 121 in the optical axis direction may be 15 microns (μm) or less. The average thickness t of the light-shielding region 121 in the optical axis direction may be an average value of thicknesses measured in a direction perpendicular to the surface of the rib portion 120, and for example, an arithmetic mean of thicknesses measured in 10 points of a conceptual circuit connecting a position of ½ of a maximum length of the rib portion 120 in the radial direction with an equal distance.

In the lens 100' according to the modified example, as illustrated in FIG. 3, a light-shielding region 121' may be disposed only on one surface or in both surfaces of the rib portion 120' in the optical axis direction. For example, the light-shielding region 121' may not be further disposed on an inner side of the surface of the rib portion 120 in the radial direction. In the lens 100" according to another modified example and the lens 100''' according to another modified example, as in FIGS. 4 and 5, the light-shielding regions 121" and 121''' may be disposed on a partial region of one surface of the rib portion 120" and 120'' in the optical axis direction, or a partial region of both surfaces. Each of these partial regions may have an almost ring shape when viewed on a plane. The light-transmitting regions 122', 122" and 122''' may also be modified according to the modification of the light-shielding regions 121', 121", and 121'''. However, these modifications are merely examples, and the light transmitting region and the light-shielding region may be modified in different forms.

The light-shielding region 121 may include a dye. For example, the light-shielding region 121 of the lens 100 may be colored using a light-shielding dye. In the example embodiment, "dye" may refer to a colorant having solubility in a solvent, and may refer to a component distinct from a pigment not dissolved in a solvent and present in a dispersed state. Generally, a method of forming a light-shielding portion by forming a coating layer including a pigment on the surface of the rib portion of the lens may be used. However, in the method of forming another layer, the surface of the lens may be damaged during a process of curing the coating film, and when the thickness of the coating film is not formed uniformly, weight balance of the lens may be disturbed. Differently from the above example, in the lens 100 according to an example, by forming the light-shielding region 121 by a method of coloring the rib portion 120 using a light-shielding dye, damages to the lens may be reduced, and a coating film attached to an external region of the lens may not be used, such that a lens having an excellent balance may be provided.

A concentration of the light-shielding dye included in the light-shielding region 121 of the lens 100 may decrease in a direction of being away from the surface of the rib portion 120. The configuration in which the concentration of the light-shielding dye decreases in a direction of being away from the surface of the rib portion 120 may indicate that the concentration of the light-shielding dye in a position spaced apart from the surface of the rib portion 120 by a predetermined distance may be lower than that of the surface. The spacing distance may refer to a depth corresponding to half of the average thickness of the light-shielding region 121 in a vertical distance from the surface of the rib portion 120. The concentration of the light-shielding dye may be a value measured in a position in which the thickness of the above light-shielding region 121 is measured, and may be detected through Raman analysis. The lens 100 according to an example is colored by dissolving a predetermined dye in a predetermined solvent, and by forming the light-shielding region 121 without using an external structure, the lens may have an excellent physical balance.

The type of the light-shielding dye included in the light-shielding region 121 of the lens 100 is not limited to any particular example, and for example, a colored or dark-colored dye may be used. For example, although not limited thereto, at least one of anthraquinone-based dye, benzoquinone-based dye, perylene-based dye, phthalocyanine-based dye, quinacridone-based pigment, azo-based dye, and diphenylmethane-based dye may be used, but an example embodiment thereof is not limited thereto. Also, a single type of dye may be used as the dye, or a combination of two or more types of dyes may be used. A mixed dye of an azo dye and an anthraquinone dye may be used as the light-shielding dye applied to the lens 100, but an example embodiment thereof is not limited thereto.

The light-shielding dye applied to the lens 100 may be a non-polar dye. In the example embodiment, "non-polar" may indicate that a relative positive charge (+) and/or a negative charge (−) does not occur because charge separation does not occur, and may refer to properties other than polarity. Also, in the example embodiment, "polarity" may refer to properties of having a dipole or more multiple poles due to the biasing of charges within a molecule, and may refer to properties of having a relative positive charge (+) and/or negative charge (−). The lens 100 according to an example may have high solubility in a solvent by applying a non-polar dye as a light-shielding dye, thereby effectively forming the light-shielding region 121 of the lens.

The non-polar dye may include a non-polar functional group such as an alkyl group or a phenyl group as a functional group. In this case, the non-polar dye may include only a non-polar functional group and may not include a polar functional group. However, the non-polar dye may include a portion of polar functional groups such as an amine group, a hydroxyl group, a carboxyl group, a ketone group, and an aldehyde group. In this case, the number of polar functional groups included in the non-polar dye may be three or less in terms of having non-polar properties. For example, the non-polar dye may include a non-polar functional group and may further include 3 or less amine groups.

The type of the non-polar dye is not limited to any particular example, and, for example, a colored or dark non-polar dye may be used. As examples of non-polar dyes, although not limited thereto, at least one non-polar dye from among non-polar anthraquinone-based dyes, non-polar benzoquinone-based dyes, non-polar perylene-based dyes, non-polar phthalocyanine-based dyes, non-polar quinacridone-based pigments, non-polar azo-based dyes, non-polar diphenylmethane-based dyes may be used, but an example embodiment thereof is not limited thereto. Also, as the non-polar dye, a single type of non-polar dye may be used, but a combination of two or more types of non-polar dye may be used. A mixed dye of a non-polar azo dye and a non-polar anthraquinone dye may be used as the light-shielding dye applied to the lens 100, but an example embodiment thereof is not limited thereto.

The light-shielding region 121 may include an ester-based compound and a hydrocarbon-based compound. The ester-based compound and the hydrocarbon-based compound may be distributed in the light-shielding region 121 of the lens 100, and may be included in the cross-linked structure formed by the polycarbonate-based compound and/or the polyolefin-based compound, for example. In the example embodiment, the term "cross-linked structure" may refer to a structure formed by cross-linking between molecules, and the term "cross-linked" may refer to forming a network structure through chemical/physical bonding such as a covalent bond, an ionic bond, a Van der Waals bond, or hydrogen bonding between molecules.

The ester-based compound may include a glycol ether acetate compound. In the example embodiment, "glycol ether acetate compound" may refer to a compound including a glycol ether group and an acetate group. For example, a glycol ether acetate compound may include at least one of propylene gylcol monomethyl ether acetate (PGMEA), ethylene glycol monobutyl ether acetate, and diethylene glycol monoethyl ether acetate, and may include propylene glycol monomethyl ether acetate, but an example embodiment thereof is not limited thereto.

The hydrocarbon-based compound may include a saturated hydrocarbon compound. In the example embodiment, "saturated hydrocarbon compound" may refer to a hydrocarbon compound which does not include an unsaturated bond. For example, a saturated hydrocarbon compound may include $CH_4$ (methane), $C_2H_6$ (ethane), $C_3H_8$ (propane), $C_4H_{10}$ (butane), $C_5H_{12}$ (pentane), $C_6H_{12}$ (hexene), $C_6H_{14}$ (hexane), $C_7H_{16}$ (heptane), $C_8H_{18}$ (octane), $C_9H_{20}$ (nonane), $C_{10}H_{22}$ (decane), $C_{11}H_{24}$ (undecane), $C_{12}H_{26}$ (dodecane) and the like. The hydrocarbon-based compound may be a saturated hydrocarbon compound, and may include a saturated hydrocarbon chain compound, or may include a C6-C10 saturated hydrocarbon chain compound, but an example embodiment thereof is not limited thereto. The C6-C10 saturated hydrocarbon chain compound may include, for example, at least one of hexane, heptane, and decane, but an example embodiment thereof is not limited thereto.

The ester-based compound and the hydrocarbon-based compound may be an organic solvent used to color the light-shielding region 121. As described above, the lens 100 according to an example may include a polycarbonate-based compound and/or a polyolefin-based compound. When the lens 100 including such a compound is in contact with an organic solvent including an ester-based compound and a hydrocarbon-based compound, the organic solvent may swell the surface of the lens 100. In this case, the nonpolar dye may permeate through the surface of the lens 100 swelled by the organic solvent and the light-shielding region 121 may be formed. In particular, when an ester-based compound and a hydrocarbon-based compound are mixed and used as an organic solvent, two materials having different polarities, such as a polycarbonate-based compound and a polyolefin-based compound, may swell. For example, an ester-based organic solvent may easily swell a polycarbonate-based material, and a hydrocarbon-based organic solvent may easily swell a polyolefin-based material.

Generally, when a lens is dyed to block light or control a path of light, a method of dyeing by dispersing a pigment in a dispersion medium such as water may be used. However, when a lens is dyed using a dispersed pigment, it may be difficult to dye depending on properties of the lens and properties of the solvent, and the degree of dyeing may be low, and light may not be effectively blocked, such that flare or ghosting may occur. For example, when a hydrophobic lens is dyed using a dispersed pigment in which the pigment is dispersed in a dispersion medium, dyeing may need to be performed at high temperature for a long time or a carrier such as trichlorobenzene or dichlorobenzene may need to be added to the dyeing solution. In this case, the lens may be deformed and optical properties may be deteriorated. Differently from the above example, in the example embodiment, by dissolving the non-polar dye in the above-mentioned mixed organic solvent and dying the light-shielding region 121 of the lens 100 using the solvent, the coloring of the dye may improve even when dyeing is performed at a low temperature for a short time. Also, light transmittance of the lens 100 may be greatly reduced in the dyed region, such that flare or ghost phenomenon may be prevented, and deformation of the lens 100 may be prevented.

The light-shielding region 121 may be formed using a dyeing solution in which the aforementioned non-polar dye is dissolved in the aforementioned mixed organic solvent, and may be dyed by immersing the lens 100 in this dyeing solution, or by applying such a dyeing solution to the lens 100, for example, but an example embodiment thereof is not limited thereto. For example, the lens 100 may be colored by forming a coating layer on the surface of the lens 100 and dipping the lens 100 in a dyeing solution. The coloring may be selectively blackened only in the region in which the coating layer is not formed. For example, the blackening may be performed only on at least a partial region of the rib portion 120 other than the optical portion 110 of the lens 100. A colored solvent may swell the polycarbonate-based and/or polyolefin-based optical polymer, and the colored dye may permeate into the swollen polymer, thereby forming a colored layer. In the dyeing solution, the concentration of the non-polar dye to the solvent is not limited to any particular example, and may be 0.01 wt % or more and/or 20 wt % or less, but an example embodiment thereof is not limited thereto. As for the dyeing solution, the coloring rate may be controlled by adjusting a mixing ratio of the above-described mixed organic solvent, that is, for example, a mixing ratio of the ester-based compound and the hydrocarbon-based compound.

When the lens 100 is dyed by being immersed in a dyeing solution, the dyeing may be performed at a temperature of 50° C. or less. For example, the dyeing may be performed at 50° C. or less, 45° C. or less, 44° C. or less, 43° C. or less, 42° C. or less, 41° C. or less, or 40° C. or less, but an example embodiment thereof is not limited thereto. When the lens 100 is immersed in a solvent in such a temperature condition, the time required for coloring the non-polar dye may be reduced without damaging the lens 100, thereby having an advantageous effect on productivity. A lower limit of the temperature is not limited to any particular example, and may be, for example, 15° C. or higher, but an example embodiment thereof is not limited thereto.

The aforementioned dye component and organic solvent component included in the colored region 121 of the lens 100 may be detected through GC-MS analysis or the like.

Lens Assembly

Figure 6:
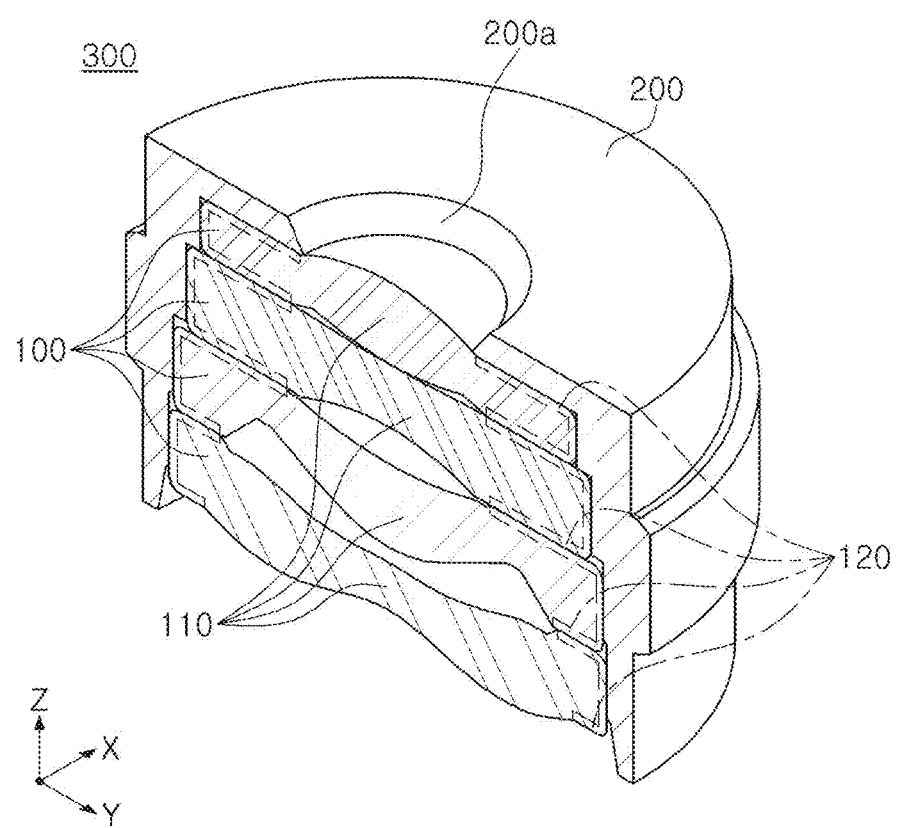
FIG. 6 is a perspective diagram illustrating a lens assembly according to an example embodiment of the present disclosure.

FIG. 6 is a perspective diagram illustrating a lens assembly according to an example embodiment.

Referring to the drawings, a lens assembly 300 according to an example may include a lens barrel 200 including an internal space, and one or more lenses 100 stacked along the optical axis in the internal space of the lens barrel 200. The lens 100 may include an optical portion 110 and a rib portion 120 extending to an external side of the optical portion 110 in a radial direction, and the rib portion 120 may include a light transmitting region 122 and a light-shielding region 121.

One or more lenses 100 may be stacked along the optical axis and may be disposed in the internal space of the lens barrel 200. A plurality of lenses 100 may be provided, and the rib portion 120 of each of the plurality of lenses 100 may be in contact with a rib portion 120 of an adjacent lens 100. Also, each of the plurality of lenses 100 may be in contact with an inner circumferential surface of the lens barrel 200. The number of the plurality of lenses 100 is not limited to any particular example, and optical properties such as refractive index of each of the plurality of lenses 100 may be the same or different.

The detailed description of the lens 100 is the same as in the aforementioned example embodiment, and the overlapping description will not be provided. The lenses 100', 100", and 100''' according to the modified examples may also be applied to the lens assembly 300.

The lens barrel 200 may have a hollow cylindrical shape, and a lens hole 200a for transmitting light may be formed through one surface of the lens barrel 200.

EXPERIMENTAL EXAMPLE

Experimental Example 1

A cycloolefin copolymer resin lens was used as a lens, a mixture of a non-polar anthraquinone-based dye and a non-polar azo-based dye was used as a light-shielding dye, and a mixed solvent in which propylene glycol monomethyl ether acetate and heptane were mixed in a ratio of 3:1 were used as an organic solvent. A dyeing solution was prepared by dissolving the dye in a solvent at a concentration of 1 wt % or more and 20 wt % or less, that is, for example, 10 wt %, a lens was immersed in the dyeing solution, and a light-shielding region was formed. A dyeing temperature of the dyeing solution was about 35° C., a light-shielding region was formed by immersing the lens for about 2 minutes, the lens was washed with water and was dried at about 80° C. for about 30 minutes, thereby obtaining a lens having a light-shielding region.

Experimental Example 2

A lens having a light-shielding region was formed in the same manner as in experimental example 1, other than the configuration in which the lens was immersed for about 4 minutes.

Experimental Example 3

A lens having a light-shielding region was formed in the same manner as in experimental example 1, other than the configuration in which the lens was immersed for about 6 minutes.

Figure 7:
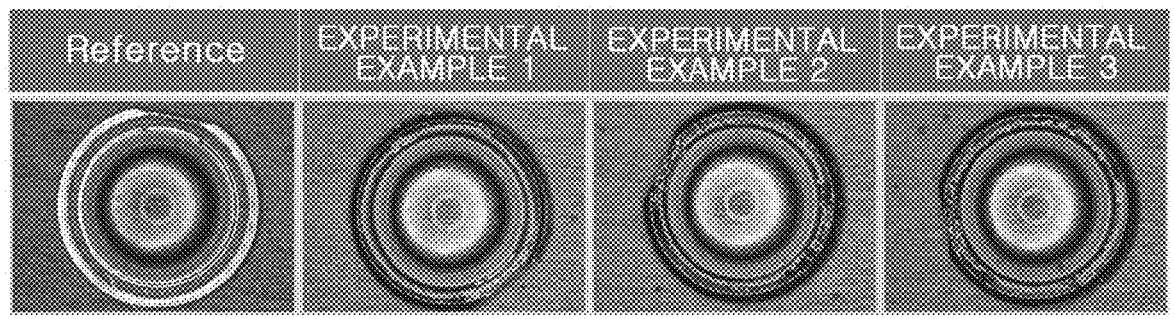
FIG. 7 shows images of results of coloring in experimental examples 1 to 3.
Figure 8:
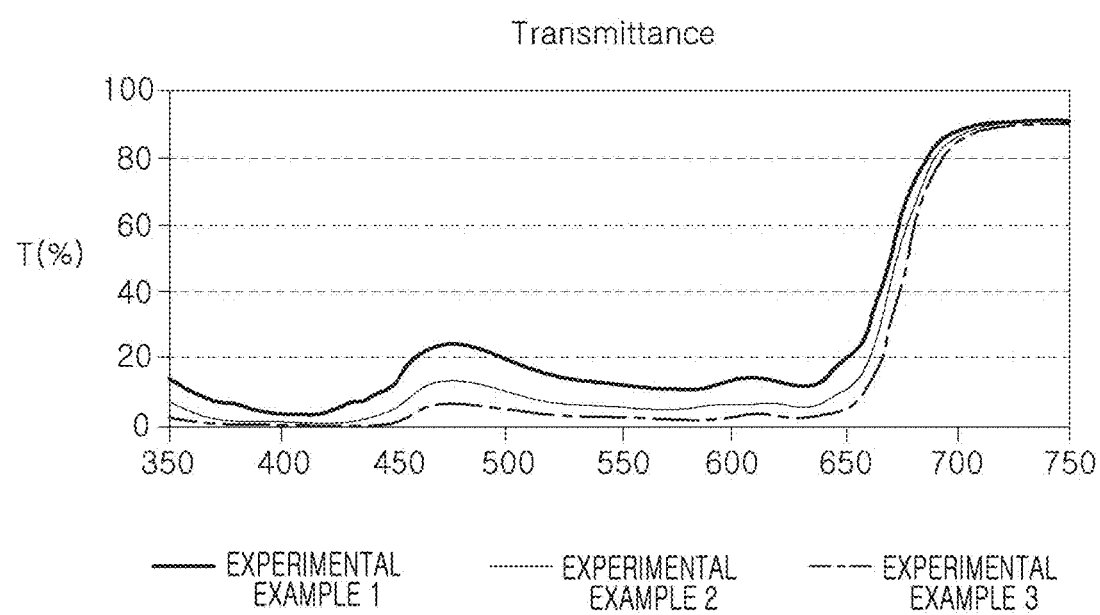
FIG. 8 shows graphs illustrating transmittance of each wavelength in experimental examples 1 to 3.

FIG. 7 shows images of results of coloring in experimental examples 1 to 3. FIG. 8 shows graphs illustrating transmittance of each wavelength in experimental examples 1 to 3.

Referring to the drawings, it is indicated that, as compared with the reference, in experimental examples 1 to 3, a light-shielding region having an excellent light-shielding rate was formed in the cycloolefin copolymer resin lens. Also, maximum transmittances for light in the range of 400 nm to 650 nm in experimental examples 1 to 3 were about 24.0%, about 13.2%, and about 6.7%, respectively, and it is indicated that the longer the immersion time, the better the light-shielding rate may be.

Experimental Example 4

A mixed solvent in which propylene glycol monomethyl ether acetate and heptane were mixed in a ratio of 1:1 was used, and a lens having a light-shielding region was formed in the same manner as in experimental example 1 other than the configuration in which the lens was immersed for about 10 minutes.

Experimental Example 5

A lens having a light-shielding region was formed in the same manner as in experimental example 4, other than the configuration in which the lens was immersed for about 20 minutes.

Figure 9:
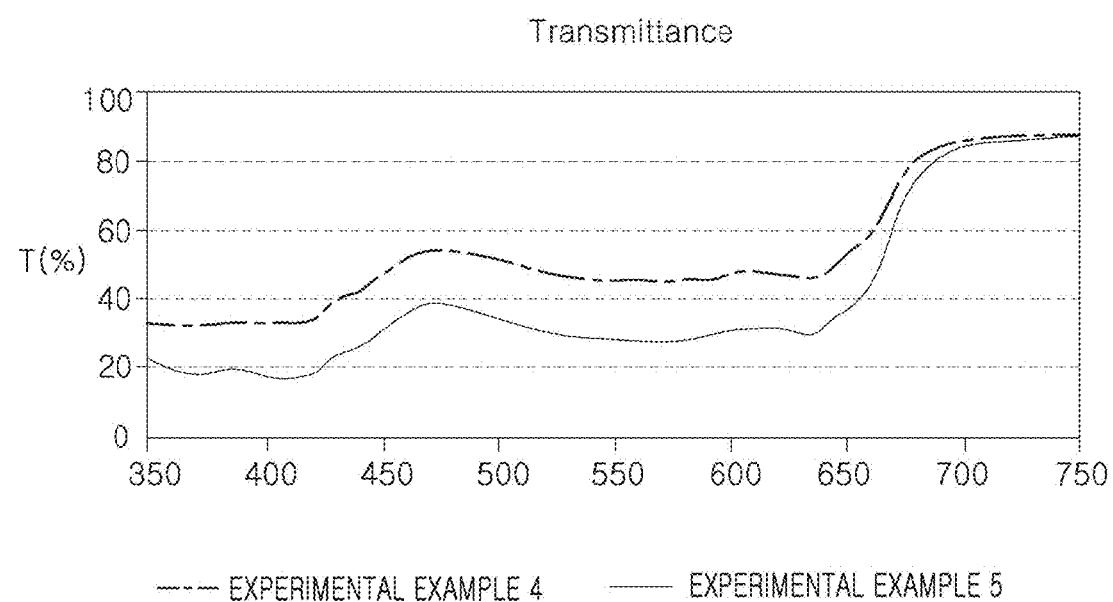
FIG. 9 shows graphs illustrating transmittance of each wavelength in experimental examples 4 and 5.

FIG. 9 shows graphs illustrating transmittance of each wavelength in experimental examples 4 and 5.

Referring to the drawings, as compared with experimental examples 1 to 3, it is indicated that the coloring rate may be controlled when the mixing ratio of the mixed solvent is adjusted. Also, maximum transmittances for light in the range of 400 nm to 650 nm in experimental examples 4 and 5 were about 54.0% and about 38.8%, respectively, and it is indicated that the longer the immersion time, the better the light-shielding rate may be.

Experimental Example 6

A lens in which a light-shielding region was formed was obtained in the same manner as in experimental example 1 other than the configuration in which a polycarbonate resin lens was used as the lens, a single solvent of propylene glycol monomethyl ether acetate was used, and the lens was immersed for about 5 minutes.

Experimental Example 7

A polycarbonate resin lens was used as a lens, and a lens having a light-shielding region was formed in the same manner as in experimental example 1, other than the configuration in which the lens was immersed for a time of about 5 minutes.

Experimental Example 8

A lens having a light-shielding region was formed in the same manner as in experimental example 7, other than the configuration in which the dyeing temperature was about 40° C.

Figure 10:
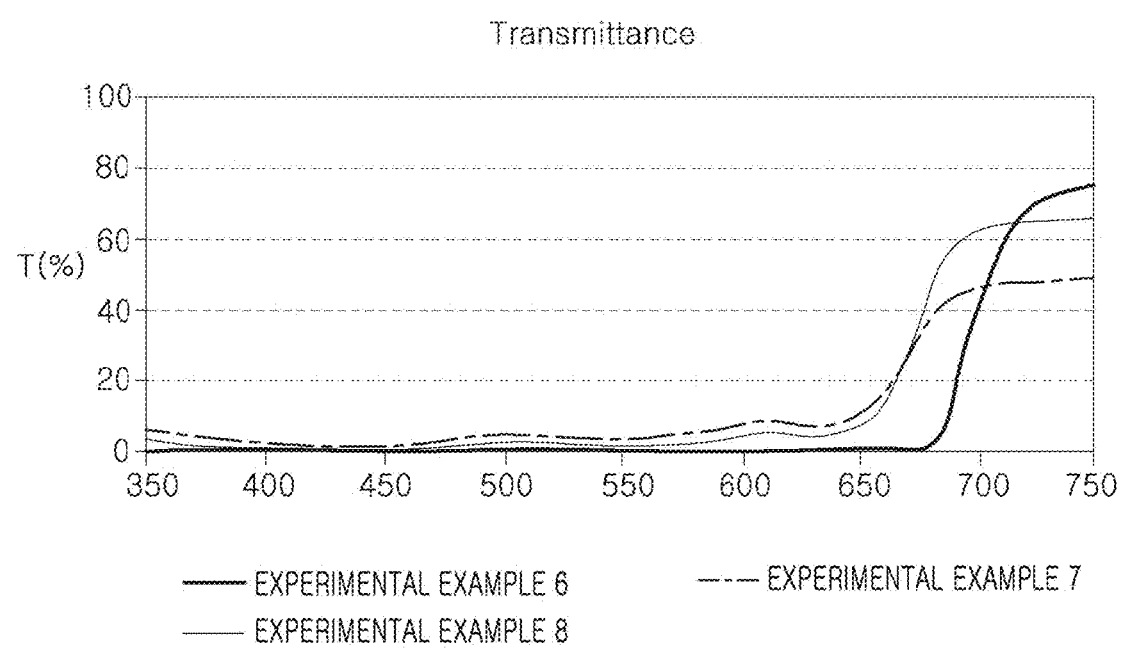
FIG. 10 presents graphs illustrating transmittance for each wavelength in experimental examples 6 to 8.

FIG. 10 presents graphs illustrating transmittance for each wavelength in experimental examples 6 to 8.

Referring to the drawings, even when a mixed solvent is used as in experimental examples 7 and 8, an excellent light-shielding region may be formed similarly to experimental example 6 using only propylene glycol monomethyl ether acetate, which may easily swell the polycarbonate resin lens. Also, the maximum transmittances for light in the range of 400 nm to 650 nm in experimental examples 7 and 8 were about 10.2% and about 6.4%, respectively, and it is indicated that the higher the immersion temperature, the better the light-shielding rate may be.

Experimental Example 9

A lens having a light-shielding region was formed in the same manner as in experimental example 1, other than the configuration in which decane was used instead of heptane.

Figure 11:
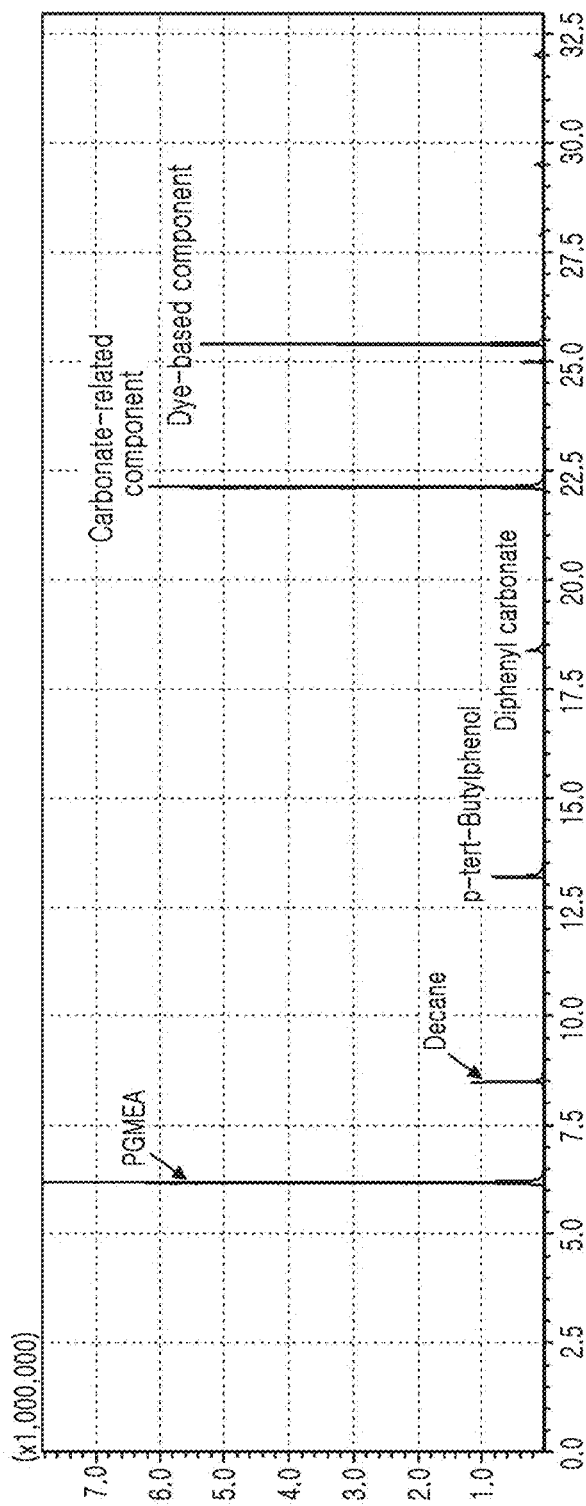
FIG. 11 is a graph illustrating a result of gas chromatography-mass spectroscopy (GC-MS) component analysis in experimental example 9.
Figure 12:
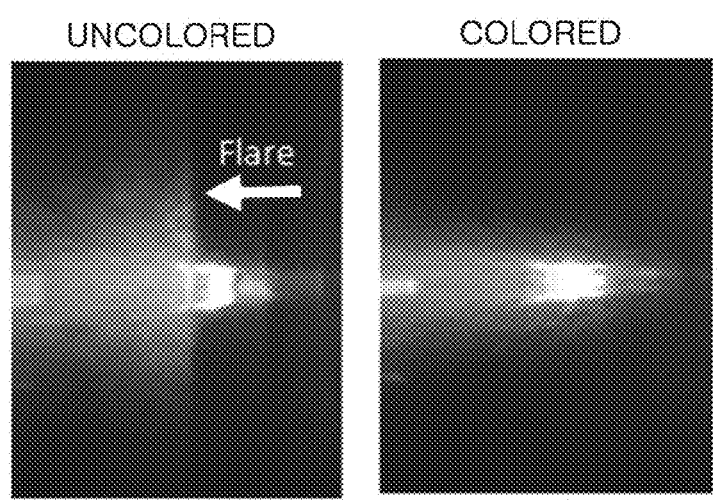
FIG. 12 shows images of result of flare evaluation in experimental example 9.

FIG. 11 is a graph illustrating a result of GC-MS component analysis in experimental example 9. FIG. 12 shows images of result of flare evaluation in experimental example 9.

Referring to the drawings, it is indicated that it is difficult to dry the lens at a high temperature due to deformation, such that a solvent component may be detected during analysis of a colored region, that is, a light-shielding region.

Also, it is indicated that the effect of improving flare after coloring the lens was excellent.

Experimental Example 10

A lens having a light-shielding region was formed in the same manner as in experimental example 2, other than the configuration in which decane was used instead of heptane.

Experimental Example 11

A lens having a light-shielding region was formed in the same manner as in experimental example 10, other than the configuration in which the lens was immersed for about 6 minutes.

Experimental Example 12

A lens having a light-shielding region was formed in the same manner as in experimental example 10, other than the configuration in which the lens was immersed for about 8 minutes.

Figure 13:
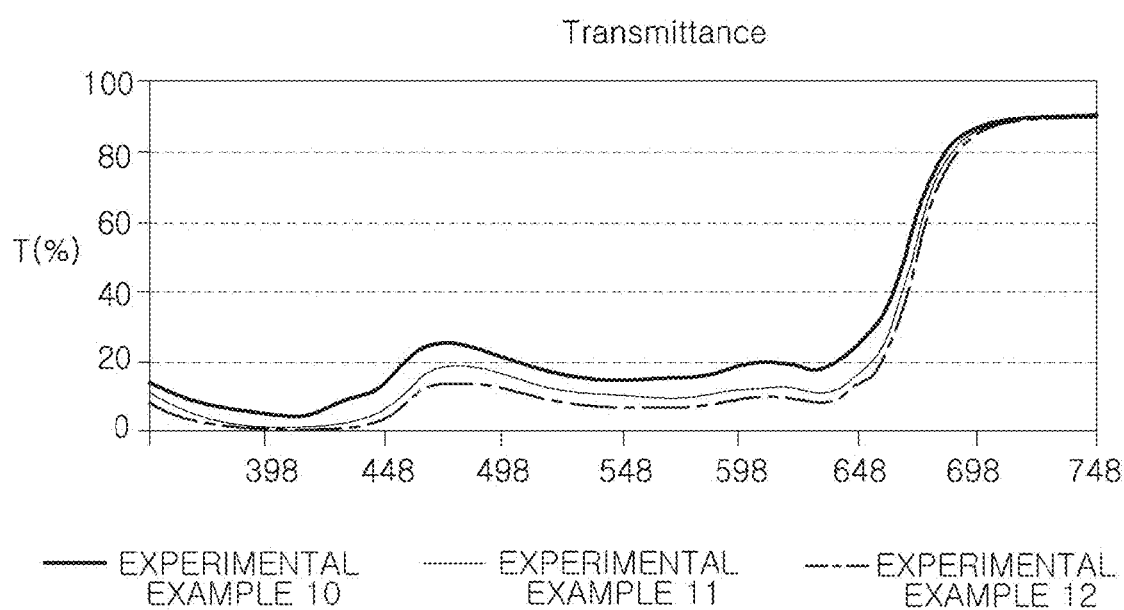
FIG. 13 presents graphs illustrating transmittance of each wavelength in experimental examples 10 to 12.

FIG. 13 presents graphs illustrating transmittance of each wavelength in experimental examples 10 to 12.

Referring to the drawings, in experimental examples 10 to 12, it is indicated that a light-shielding region having an excellent light-shielding rate was formed in the cycloolefin copolymer resin lens. Also, the maximum transmittances for light in the range of 400 nm to 650 nm of experimental examples 10 to 12 were about 25.6%, about 18.6%, and about 14.0%, respectively, and the longer the immersion time, the better the light-shielding rate may be.

Experimental Example 13

A lens in which a light-shielding region was formed in the same manner as in experimental example 10 was formed other than the configuration in which a polycarbonate resin lens was used as the lens, a single solvent of propylene glycol monomethyl ether acetate was used, and the lens was immersed for about 5 minutes.

Experimental Example 14

A lens in which a light-shielding region was formed in the same manner as in experimental example 10 was formed other than the configuration in which a polycarbonate resin lens was used as a lens, and the lens was immersed for about 5 minutes.

Experimental Example 15

A lens having a light-shielding region was formed in the same manner as in experimental example 14, other than the configuration in which the dyeing temperature was about 40° C.

Figure 14:
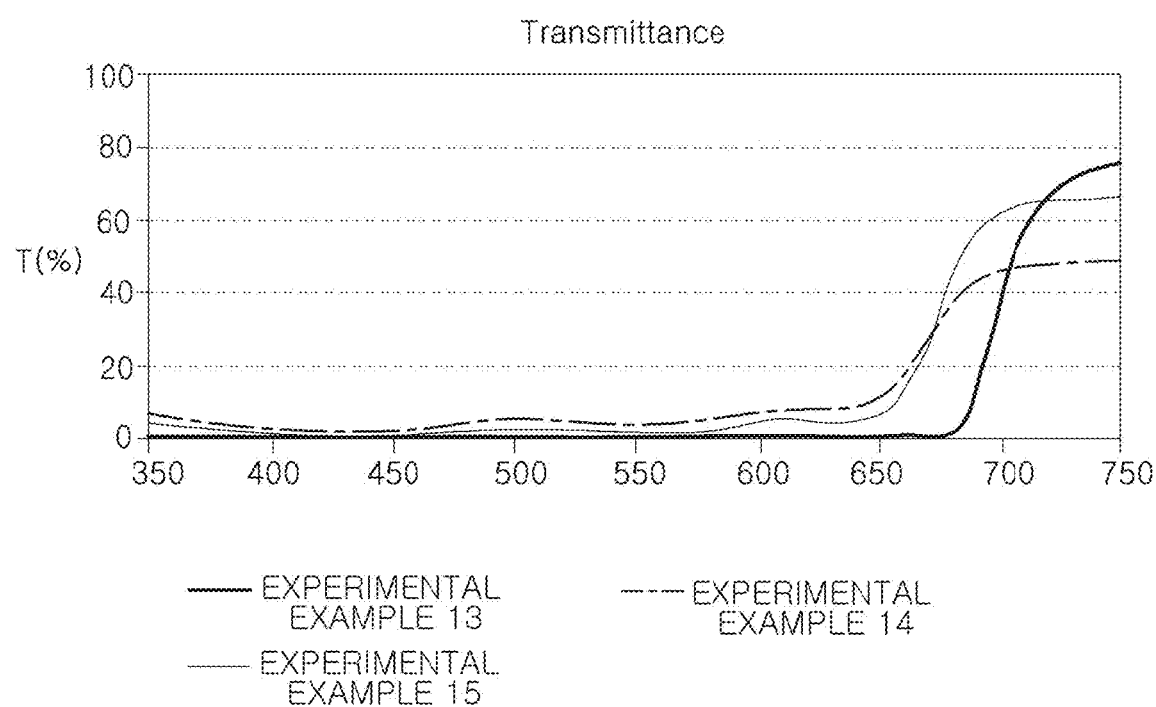
FIG. 14 shows graphs illustrating transmittance of each wavelength in experimental examples 13 to 15.

FIG. 14 shows graphs illustrating transmittance of each wavelength in experimental examples 13 to 15.

Referring to the drawings, even when a mixed solvent is used as in experimental examples 14 and 15, an excellent light-shielding region may be formed similarly to experimental example 13 in which propylene glycol monomethyl ether acetate, which may easily swell the polycarbonate resin lens, is used alone. Also, the maximum transmittances for light in the range of 400 nm to 650 nm of experimental examples 14 and 15 were about 10.2% and about 6.4%, respectively, and it is indicated that the higher the immersion temperature, the better the light-shielding rate may be.

According to the aforementioned example embodiments, a lens in which at least a portion of the rib portion of the polycarbonate-based and/or polyolefin-based optical polymer is blackened, and a lens assembly including the same may be provided.

Also, a lens which may prevent flare or ghosting, and a lens assembly including the same may be provided.

In the example embodiments, a cross-sectional surface may refer to a cross-sectional shape of when an object is vertically cut, or a cross-sectional shape of when an object is viewed from the side. Also, "being on a plane" may be a shape of when an object is horizontally cut, or a planar shape of when an object is viewed from the top or the bottom.

In the example embodiments, the terms "side portion," "side surface," and the like, may be used to refer to a surface formed taken in right/left directions with reference to a cross-sectional surface in the diagrams for ease of description, the terms "upper side," "upper portion," "upper surfaces," and the like, may be used to refer to a surface formed in an upward direction with reference to a cross-sectional surface in the diagrams for ease of description, and the terms "lower side," "lower portion," "lower surface," and the like, may be used to refer to a surface formed in a downward direction. The notion that an element is disposed on a side region, an upper side, an upper region, or a lower resin may include the configuration in which the element is directly in contact with an element configured as a reference in respective directions, and the configuration in which the element is not directly in contact with the reference element. The terms, however, may be defined as above for ease of description, and the scope of right of the example embodiments is not limited to any particular example to the above terms.

In the example embodiments, the term "connected" may not only refer to "directly connected" but also include "indirectly connected" by means of an adhesive layer, or the like. Also, the term "electrically connected" may include both of the case in which elements are "physically connected" and the case in which elements are "not physically connected." Further, the terms "first," "second," and the like may be used to distinguish one element from the other, and may not limit a sequence and/or an importance, or others, in relation to the elements. In some cases, a first element may be referred to as a second element, and similarly, a second element may be referred to as a first element without departing from the scope of right of the example embodiments.

In the example embodiments, the term "example embodiment" may not refer to one same example embodiment, and may be provided to describe and emphasize different unique features of each example embodiment. The above suggested example embodiments may be implemented do not exclude the possibilities of combination with features of other example embodiments. For example, even though the features described in one example embodiment are not described in the other example embodiment, the description may be understood as relevant to the other example embodiment unless otherwise indicated.

An expression used in the singular encompasses the expression of the plural, unless it has a clearly different meaning in the context.

While specific example embodiments have been shown and described above, it will be apparent after an understanding of this disclosure that various changes in form and details may be made in these examples without departing from the spirit and scope of the claims and their equivalents.

The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A lens, comprising:
an optical portion; and
a rib portion extending to an external side of the optical portion in a radial direction and comprising a light transmitting region and a light-shielding region,
wherein the light-shielding region comprises an ester-based compound and a hydrocarbon-based compound, and
wherein the hydrocarbon-based compound comprises a saturated hydrocarbon compound.

2. The lens of claim 1, wherein the saturated hydrocarbon compound comprises a C6-C10 saturated hydrocarbon chain compound.

3. The lens of claim 2, wherein the C6-C10 saturated hydrocarbon chain compound comprises at least one of hexane, heptane, and decane.

4. The lens of claim 1, wherein the ester-based compound comprises a glycol ether acetate compound.

5. The lens of claim 4, wherein the glycol ether acetate compound comprises at least one of propylene glycol monomethyl ether acetate, ethylene glycol monobutyl ether acetate, and diethylene glycol monoethyl ether acetate.

6. The lens of claim 1, wherein the light-shielding region further comprises a light-shielding dye.

7. The lens of claim 6, wherein the light-shielding dye comprises at least one non-polar dye of a non-polar azo dye and a non-polar anthraquinone dye.

8. The lens of claim 1, wherein the lens comprises at least one of a polycarbonate-based compound and a polyolefin-based compound.

9. The lens of claim 1, wherein the light-shielding region is disposed in the rib portion.

10. The lens of claim 9, wherein the light-shielding region is disposed on an inner side of at least one surface of the rib portion in an optical axis direction.

11. The lens of claim 10, wherein the light-shielding region is disposed on an inner side of a partial region of at least one surface of the rib portion in the optical axis direction.

12. The lens of claim 10, wherein the light-shielding region is further disposed on an inner side of a surface of the rib portion in the radial direction.

13. A lens assembly, comprising:
a lens barrel comprising an internal space; and
one or more lenses stacked along an optical axis in the internal space of the lens barrel,
wherein at least one lens of the one or more lenses comprises an optical portion and a rib portion extending to an external side of the optical portion in a radial direction and comprising a light transmitting region and a light-shielding region,
wherein the light-shielding region comprises an ester-based compound and a hydrocarbon-based compound, and
wherein the hydrocarbon-based compound comprises a saturated hydrocarbon compound.

14. The lens assembly of claim 13,
wherein the at least one lens comprises a polycarbonate-based component or a polyolefin-based compound, and
wherein the light-shielding region comprises propylene glycol monomethyl ether acetate and hexane, heptane, or decane.

15. The lens assembly of claim 14, wherein the light-shielding region further comprises at least one non-polar dye of a non-polar azo dye and a non-polar anthraquinone dye.

16. The lens assembly of claim 13, wherein the light-shielding region is disposed in the rib portion.

17. A lens, comprising:
an optical portion; and
a rib portion extending to an external side of the optical portion in a radial direction and comprising a light transmitting region and a light-shielding region,
wherein the light-shielding region comprises a dye disposed in the rib portion, and
wherein a concentration of the dye decreases in a direction away from a surface of the rib portion.

18. The lens of claim 17, wherein the light-shielding region is disposed on an inner side of one surface of the rib portion in an optical axis direction, and
wherein the light transmitting region and the light-shielding region are disposed in sequence in the optical axis direction.

19. The lens of claim 17, wherein the light-shielding region comprises an ester-based compound and a hydrocarbon-based compound, and
wherein the hydrocarbon-based compound comprises a saturated hydrocarbon compound.

* * * * *